United States Patent
Yamaguchi et al.

(10) Patent No.: US 7,271,287 B2
(45) Date of Patent: Sep. 18, 2007

(54) PROCESS FOR PRODUCING AROMATIC HYDROXYCARBOXYLIC ACIDS

(75) Inventors: Tatsuaki Yamaguchi, Narashino (JP); Koichi Sato, Yokohama (JP)

(73) Assignees: Chiba Institute of Technology, Chiba (JP); Nippon Oil Corporation, Tokyo (JP)

( * ) Notice: Subject to any disclaimer, the term of this patent is extended or adjusted under 35 U.S.C. 154(b) by 50 days.

(21) Appl. No.: 11/270,716

(22) Filed: Nov. 9, 2005

(65) Prior Publication Data
US 2006/0122420 A1 Jun. 8, 2006

(30) Foreign Application Priority Data
Dec. 3, 2004 (JP) .............................. 2004-351020

(51) Int. Cl.
*C07C 51/15* (2006.01)
*C07C 51/00* (2006.01)

(52) U.S. Cl. ...................................... 562/424; 562/406

(58) Field of Classification Search ................ 562/424, 562/406
See application file for complete search history.

(56) References Cited

U.S. PATENT DOCUMENTS 4,260,802 A * 4/1981 Hallgren ...................... 560/71
4,376,867 A 3/1983 Jansen et al.

* cited by examiner

*Primary Examiner*—Joseph McKane
*Assistant Examiner*—Lalitha Nagubandi
(74) *Attorney, Agent, or Firm*—Akin Gump Strauss Hauer & Feld LLP

(57) ABSTRACT

There is provided a process for producing an aromatic hydroxycarboxylic acid which is capable of suppressing the formation of by-products and enhancing the selectivity of the intended product and is free from any purifying step. The process is characterized in that it is obtained by reacting an alkali metal salt of an aromatic hydroxy compound and carbon dioxide in a non-proton polar solvent in the presence of a solid basic catalyst.

5 Claims, No Drawings

PROCESS FOR PRODUCING AROMATIC HYDROXYCARBOXYLIC ACIDS

BACKGROUND OF THE INVENTION

The present invention relates to an improved process for producing aromatic hydroxycarboxylic acids.

Aromatic hydroxycarboxylic acids are important as antiseptics or preservatives for foods and cosmetics, or raw materials or intermediates of pigments, dyes, liquid crystals, liquid crystalline polymers, medicines, and agricultural chemicals and are generally produced by a solid-gas phase reaction known as the Kolbe-Schmitt reaction wherein an alkali metal salt of an aromatic compound having a phenolic hydroxyl group is reacted with carbon dioxide.

However, in the case where this reaction is conducted in a single step, there arises a problem concerning the formation of by-products. For example, in the case of salicylic acid synthesis, p-hydroxybenzoic acid and 4-hydroxy-isophthalic acid are by-produced in the total amount of about 0.4 percent by mole (see U.S. Pat. No. 4,376,867). Therefore, in order to obtain an aromatic hydroxycarboxylic acid at high purity, for example, a multi-step process is required because it is necessary to remove such by-products by incorporating to the reaction process a refining step such as sublimation.

BRIEF SUMMARY OF THE INVENTION

It is an object of the present invention to provide a process for producing an aromatic hydroxycarboxylic acid, which is capable of enhancing the selectivity of the intended product by suppressing the formation of by-products without the necessity of any refining process.

The present invention was achieved as a result of extensive research and study made by the inventors thereof.

That is, according to the present invention, there is provided a process for producing an aromatic hydroxycarboxylic acid wherein it is obtained by reacting an alkali metal salt of an aromatic hydroxy compound and carbon dioxide in a non-proton polar solvent in the presence of a solid basic catalyst.

DETAILED DESCRIPTION OF THE INVENTION

The present invention will be described in more detail below.

The aromatic hydroxy compound which may be used in the present invention may be any compound as long as it has one or more hydroxyl groups bonding to the aromatic ring (aromatic hydrocarbon ring, aromatic heterocyclic ring). Examples of the aromatic hydroxy compound include monovalent phenols such as phenol, cresol (o-cresol, m-cresol, p-cresol), xylenol (2,3-xylenol, 3,5-xylenol), carvacrol, thymol, naphthol ($\alpha$-naphthol, $\beta$-naphthol), anthrol, phenanthrol, 2,5-diphenylphenol, 8-quinolinol, indole-5-ol and 3-hydroxythiophene; divalent phenols such as pyrocatechol, resorcinol, hydroquinone, 2,2'-biphenyldiol and 4,4'-biphenyldiol; and trivalent phenols such as pyrogallol and phloroglucinol. Alternatively, the aromatic hydroxy compound used as the raw material may be any commercially available product such as those with a purity of 98 percent. Preferred are those with few kinds of impurities and less amount of thereof.

Examples of an alkali metal used for the production of an alkali metal salt of an aromatic hydroxy compound include sodium, potassium, and lithium.

There is no particular restriction on the method of producing an alkali metal salt of an aromatic hydroxy compound. Therefore, any conventional method may be employed.

There is no particular restriction on carbon dioxide used in the present invention. Any commercial available products may be used, or alternatively those diluted with an inert gas. Preferred are those with less impurities interrupting the reaction.

Examples of the solid basic catalyst include alkaline earth metal oxides such as magnesium oxide and calcium oxide; alkali metal oxides such as sodium oxide and potassium oxide; rare earth oxides such as lanthanum oxide and yttrium oxide; hydrotalcites; and hydroxyapatite. Among these, preferred are alkaline earth metal oxides, more preferred are magnesium oxide and calcium oxide, and particularly preferred is magnesium oxide.

The ratio of the raw material, i.e., aromatic hydroxy compound to the solid basic catalyst (initial molar ratio) is from 10 to 1000, preferably from 15 to 500, and more preferably 18 to 100.

Examples of the non-proton polar solvent include ketones such as acetone, methyl ethyl ketone, methyl isobutyl ketone and cyclohexanone; ethers such as tetrahydrofuran, dioxane, 1,2-dimethoxyethane, diphenyl ether, diethyl ether and diisopropyl ether; amides such as dimethylformamide, dimethylacetoamide and N-methyl-2-pyrrolidone; nitrites such as acetonitrile, propionitrile and benzonitrile; carbonates such as ethylene carbonate and diphenyl carbonate; nitro-based compounds such as nitrobenzene, nitrotoluene and nitroanisole; and organic sulfuric oxides such as dimethyl sulfoxide, tetramethylene sulfolane and dimethyl sulfolane. Among these, particularly preferred is acetonitrile.

The amount of the non-proton polar solvent to be used varies depending on the type thereof, type of the raw material, i.e., aromatic hydroxy compound, type of the solid basic catalyst and percentage of the aromatic hydroxy compound and the solid basic catalyst but is usually from 50 to 5000 parts by weight, preferably from 100 to 2000 parts by weight, and more preferably 200 to 1000 parts by weight, based on 100 parts by weight of the aromatic hydroxy compound.

The reaction temperature at which the above-described reaction is conducted is preferably from 80 to 250° C., more preferably from 150 to 220° C. The reaction temperature of lower than 80° C. is not preferable because the reaction does not proceed sufficiently. The reaction temperature of higher than 250° C. is not also preferable because by-products are formed. Furthermore, the reaction pressure is preferably from 0.05 to 25 MPa, more preferably from 0.5 to 10 MPa, and further more preferably from 2 to 5 MPa. The reaction time is preferably from 10 to 300 minutes, more preferably from 60 to 180 minutes. The reaction time of shorter than 10 minutes is not preferable because the yield is reduced while the reaction time longer than 300 minutes is not also preferable because by-products are formed.

The reaction apparatus used in the present invention is usually a metallic reaction apparatus which is capable of pressurizing.

As a result of the reaction, there is formed an aromatic hydroxycarboxylic acid corresponding to the aromatic hydroxy compound used as the raw material, or a salt of the aromatic hydroxycarboxylic acid. Such a salt may be converted to a free aromatic hydroxycarboxylic acid by a conventional method. The resulting product, i.e., aromatic hydroxycarboxlic acid or salt thereof varies in the position of the carboxyl group depending on the reaction conditions such as the reaction temperature or type of solvent, but the carboxyl group is positioned at the ortho or para position with respect to the hydroxyl group and more frequently is positioned at the ortho position.

After completion of the reaction, the reaction product may be separated and purified by any separation method such as neutralization (liberation of salt), filtration, concentration, distillation, extraction, crystallization, recrystallization, adsorption, and column chromatography or any combination thereof.

By the process of the present invention an aromatic hydroxycarboxylic acid can be selectively obtained while suppressing the formation of by-products. Particularly when the reaction is conducted using phenol as an aromatic hydroxy compound, i.e., the raw material, magnesium oxide as the solid basic catalyst, and acetonitrile as the non-proton polar solvent, salicylic acid can be obtained at a selectivity of almost 100 percent.

The present invention will be described in more detail with reference to the following examples. "Percent" herein indicates percent by mole.

EXAMPLE 1

9.6 g (100 mmol) of phenol were dissolved in 100 mL of a 1N-potassium hydroxide aqueous solution thereby preparing a phenol potassium aqueous solution. The resulting solution was dehydrated using a rotary evaporator and vacuum-dried at a temperature of 180° C. thereby obtaining water-free powdery potassium phenoxide.

1.32 g (10 mmol) of potassium phenoxide obtained above was dissolved in 10 mL of acetonitrile, and then 0.02 g of magnesium oxide was added thereto. The mixture was charged into a 50 mL internal volume electromagnetic induction type rotary autoclave. Thereafter, carbon dioxide was introduced into the autoclave to bring the pressure therein to 3 MPa. The mixture was heated to a temperature of 200° C. while being stirred and then reacted for 2 hours. After completion of the reaction, the autoclave was rapidly cooled, and the reaction product was dried using a rotary evaporator and recovered in the form of an aqueous solution by adding thereto water. The reaction product was subjected to qualitative and quantitative analyses using HPLC (High Performance Liquid Chromatography). The yield of salicylic acid was 40 percent, and the selectivity of potassium phenoxide toward salicylic acid was 100 percent.

COMPARATIVE EXAMPLE 1

1.32 g (10 mmol) of potassium phenoxide was dissolved in 10 mL of acetonitrile and charged into a 50 mL internal volume electromagnetic induction type rotary autoclave. Thereafter, carbon dioxide was introduced into the autoclave to bring the pressure therein to 3 MPa. The mixture was heated to a temperature of 200° C. while being stirred and then reacted for 2 hours. After completion of the reaction, the autoclave was rapidly cooled, and the reaction product was dried using a rotary evaporator and recovered in the form of an aqueous solution by adding thereto water. The reaction product was subjected to qualitative and quantitative analyses using HPLC. The yield of salicylic acid was 14 percent, and the selectivity of potassium phenoxide toward salicylic acid was 45 percent.

EXAMPLE 2

1.32 g (10 mmol) of potassium phenoxide was dissolved in 10 mL of tetrahydrofuran, and 0.02 g of magnesium oxide was added thereto. The mixture was charged into a 50 mL internal volume electromagnetic induction type rotary autoclave. Thereafter, carbon dioxide was introduced into the autoclave to bring the pressure therein to 3 MPa. The mixture was heated to a temperature of 200° C. while being stirred and then reacted for 2 hours. After completion of the reaction, the autoclave was rapidly cooled, and the reaction product was dried using a rotary evaporator and recovered in the form of an aqueous solution by adding thereto water. The reaction product was subjected to qualitative and quantitative analyses using HPLC. The yield of salicylic acid was 68 percent, and the selectivity of potassium phenoxide toward salicylic acid was 91 percent.

We claim:

1. A process for producing an aromatic hydroxycarboxylic acid, the method comprising reacting an alkali metal salt of an aromatic hydroxy compound and carbon dioxide in a non-proton polar solvent in the presence of a solid basic catalyst selected from the group consisting of alkaline earth metal oxides, alkali metal oxides, rare earth oxides, hydrotalcites, and hydroxyapatite.

2. The process for producing an aromatic hydroxycarboxylic acid according to claim 1 wherein said aromatic hydroxy compound is phenol.

3. The process for producing an aromatic hydroxycarboxylic acid according to claim 1 wherein said solid basic catalyst is magnesium oxide.

4. The process for producing an aromatic hydroxycarboxylic acid according to claim 1 wherein said non-proton polar solvent is acetonitrile.

5. The process for producing an aromatic hydroxycarboxylic acid according to claim 1 wherein said aromatic hydroxycarboxylic acid is salicylic acid.

* * * * *